US012562079B2

(12) United States Patent
Perkins et al.

(10) Patent No.: US 12,562,079 B2
(45) Date of Patent: Feb. 24, 2026

(54) MEDICAL DEVICE PACKAGING WITH INTEGRATED TRAINING OR TEACHING SIMULATOR

(71) Applicant: Welch Allyn, Inc., Skaneateles Falls, NY (US)

(72) Inventors: David Gregory Perkins, Skaneateles Falls, NY (US); Megan McGinn Schneider, Skaneateles Falls, NY (US); Michael John Suits, Skaneateles Falls, NY (US); Sean R. Karla, Skaneateles Falls, NY (US); Erin Jean Mickam, Skaneateles Falls, NY (US); Emmeline Marie Perkins, Skaneateles Falls, NY (US); Jonathan Quinn Hogan, Skaneateles Falls, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 925 days.

(21) Appl. No.: 17/723,823

(22) Filed: Apr. 19, 2022

(65) Prior Publication Data

US 2022/0335858 A1    Oct. 20, 2022

Related U.S. Application Data

(60) Provisional application No. 63/258,224, filed on Apr. 19, 2021.

(51) Int. Cl.
| | |
|---|---|
| *G09B 23/30* | (2006.01) |
| *A61B 50/30* | (2016.01) |
| *A61B 1/227* | (2006.01) |
| *A61B 3/12* | (2006.01) |

(52) U.S. Cl.
CPC ............. *G09B 23/30* (2013.01); *A61B 50/30* (2016.02); *A61B 1/227* (2013.01); *A61B 3/12* (2013.01)

(58) Field of Classification Search
None
See application file for complete search history.

(56) References Cited

U.S. PATENT DOCUMENTS

| | | |
|---|---|---|
| 10,861,352 B2 | 12/2020 | Perkins et al. |
| 2019/0216307 A1 | 7/2019 | Coon et al. |
| 2019/0311652 A1* | 10/2019 | Perkins ................. G09B 23/28 |

* cited by examiner

*Primary Examiner* — James B Hull
(74) *Attorney, Agent, or Firm* — Barclay Damon LLP

(57) ABSTRACT

A package is defined by an enclosure sized for retaining a medical diagnostic instrument and/or instrument supplies. A teaching aid, which simulates at least one medical target of interest, is directly integrated into the package for use with a medical diagnostic instrument. In at least one version, a sales demonstration aid is integrated with the packaging to highlight an enhanced field of view of the medical diagnostic instrument and provide a comparative field of view with other similar instruments.

18 Claims, 8 Drawing Sheets

100

144

114

110

119

154

153

140

112

151

955

160

174

180

163

MEDICAL DEVICE PACKAGING WITH INTEGRATED TRAINING OR TEACHING SIMULATOR

CROSS REFERENCE TO RELATED APPLICATIONS

This application claims priority to U.S. Ser. No. 63/258,224, filed Apr. 19, 2021 under relevant portions of 35 U.S.C. §§ 119 and 120. The above-noted document is herein incorporated by reference in its entirety.

TECHNICAL FIELD

This application is generally directed to the field of diagnostic medicine and more specifically to the integration of an anatomical training model or teaching aid that is integrated into the packaging of at least one diagnostic medical device.

BACKGROUND

Hand-held diagnostic devices are well known for examining patients as part of a wellness checkup or other medical visit. These devices include an instrument head, which is often releasably attached to the upper end of an instrument handle, the instrument head having contained optics and a contained light source powered by batteries contained in the handle or by a line powered wall system. The contained optics are aligned along a viewing axis extending through respective distal and proximal ends of the instrument head with emitted light being directed to the distal end of the instrument head and to the medical target of interest. These diagnostic devices can include otoscopes, which are typically used for examining the outer and middle ear of a patient, and ophthalmoscopes, which are typically used for examining the back of the patient's eye and more specifically the retina, optic disc, choroid and blood vessels.

Otoscopes employ a speculum tip that is releasably attached to the distal end of the instrument head to help prevent cross contamination between patients. The speculum tip is a hollow component having a substantially conical configuration including a distal tip opening. Following attachment to the body of the otoscope, the speculum tip is configured to be positioned up to a predetermined distance within the ear canal of a patient.

An ophthalmoscope is configured to view the fundus and related aspects of the eye such as the retina and the optic disc. A flexible elastomeric eye cup can be attached to the distal end of the ophthalmoscope to assist with the examination and provide a suitable working distance relative to the patient.

Training is essential in the use of these medical diagnostic devices in order to conduct an effective examination of a subject. To effectuate the training/teaching or medical students and other users of these devices, sophisticated anatomical models of the human eye and ear are available. These teaching aids are expensive, however, and often not immediately accessible for use. Proper training increases clinician confidence, diagnostic accuracy, and examination speed for a quick diagnosis.

BRIEF DESCRIPTION

Therefore and according to at least one aspect, there is provided a medical diagnostic instrument system comprising a package having an enclosure sized and configured for retaining at least one of a medical diagnostic instrument and instrument supplies, and a teaching aid configured for use with at least one medical diagnostic instrument, wherein the teaching aid is directly incorporated into the package.

In at least one version, the package includes a front wall, a rear wall, a top wall, a bottom wall and respective side walls that define the enclosure. The front wall can include one or more through openings, each opening being sized and configured to receive or be aligned with a distal end of a medical diagnostic instrument, and wherein at least one teaching image of a medical target is provided at the rear wall within the defined enclosure. According to at least one embodiment, the one or more openings are slightly angled in relation to the teaching image(s) in order to minimize the effects of glare from a light source of the medical diagnostic instrument. In at least one version, two or more through openings can be provided on the front wall of the package, each of which are suitably aligned with respective teaching images within the package enclosure based on the physical properties, such as opening size and distance to the teaching image(s), of the packaging.

In at least one version, the front wall of the package can be hingably attached at one end to permit access to the interior of the defined enclosure in order to enable removal of the diagnostic instrument from the package. According to at least one version, the one or more through openings and aligned teaching image(s) can be representative anatomical models or simulators of two or more different medical targets, (e.g., the ear and the eye), permitting training in the use of at least one of an otoscope and an ophthalmoscope.

According to at least one embodiment, the package can include a removable sleeve that covers the front wall, the rear wall and the respective side walls of the box portion. In at least one version, the sleeve and box can be used as a sales demonstration aid prior to sale. The sleeve can include a through opening formed in a front side that is aligned with an image provided on the front wall of the box portion, the image being representative of a medical target for which the packaged medical diagnostic instrument is designed to examine. According to one embodiment, the representative image presents the field of view of the packaged medical diagnostic instrument and when aligned with the opening of the sleeve, a comparative field of view is presented that is obtainable with another medical diagnostic instrument of the same type (e.g., otoscope or ophthalmoscope).

According to another aspect, there is provided a package for a medical diagnostic instrument, the package comprising an enclosure sized for retaining the medical diagnostic instrument, and a teaching aid for use with the medical diagnostic instrument, the teaching aid being incorporated as a part of the package.

The package can be defined by a box portion having a front wall, a rear wall, a top wall, a bottom wall, and respective side walls wherein the front wall is hingably attached to the top wall to permit access to the interior of the defined enclosure in order to access and remove the medical diagnostic instrument. The teaching aid includes one or more through openings, preferably formed in the front wall of the package, that are aligned with at least one teaching image provided within the defined enclosure. The one or more through openings are preferably sized to receive or be aligned with a distal or engagement end of the medical diagnostic instrument. In at least one version, the one of more through openings are angled in relation to the at least one teaching image such that glare from a light source of the medical diagnostic instrument is minimized or at least substantially reduced.

According to at least one version, the package further includes a removable sleeve portion that is sized to fit over the front wall, the rear wall and the respective side walls of the box portion. The sleeve and box portion can be used in conjunction as a sales demonstration aid prior to sale in which the sleeve can include a through opening that is aligned with a representative image of a medical target presented on the box portion of the package. The representative image can include an expected field of view of a medical target for which the packaged medical diagnostic instrument is intended to examine while the opening in the sleeve presents a reduced field of view obtainable by another medical diagnostic instrument of the same type, thus demonstrably highlighting the improved performance of the packaged device.

In at least one version, at least one teaching image can be provided directly on the inner surface of the rear wall or preferably one or more teaching images can be disposed on a one or more training cards sized for placement within the enclosure. When so disposed, the at least one teaching image is aligned with the through opening(s) formed in the front wall of the package. A plurality of training cards can be provided, each training card having a plurality of different teaching images that can be used interchangeably to simulate aspects of the medical target of interest for use with the packaged or other medical diagnostic instruments. For example and according to at least one version, one training card can include various images of both the eye and middle ear to permit training using both ophthalmoscopes and otoscopes. Teaching images can provide a number of examples of aberrant conditions or expected anatomy to improve training. According to another version, at least one of the training cards may include a visual acuity chart or a pupil sizing gauge.

According to yet another aspect, there is provided packaging for a medical diagnostic instrument comprising a box portion having an enclosure sized for retaining the medical diagnostic instrument and a removable sleeve portion. The box portion includes a front cover having a representative image of the field of view of a medical target of the packaged medical diagnostic instrument and the removable sleeve portion includes an opening that is aligned with the representative image on the box portion, the opening providing a limited field of view smaller than that of the entire representative image and depicting the field of view of a prior medical diagnostic instrument.

According to yet another aspect, there is provided a method for packaging a medical diagnostic instrument, the method comprising the steps of providing a package, the package having a front surface, a back surface, a top surface, a bottom surface and respective side surfaces defining an enclosure sized for retaining the medical diagnostic instrument. According to the herein described method, a teaching aid is directly incorporated as part of the package, the teaching aid being configured as an anatomical model configured to provide training in the use of at least one medical diagnostic instrument.

One or more through openings are provided, preferably in the front wall of the package, each opening being sized and configured to either receive or be aligned with at least one medical diagnostic instrument. Emitted light is directed from the at least one medical diagnostic instrument for viewing at least one teaching image of a medical target of interest that is disposed within the defined enclosure.

According to at least one version, the integrated teaching aid can be used with a packaged medical diagnostic instrument or in conjunction with one or more different medical diagnostic instruments and/or instrument supplies. In at least one embodiment, anatomical models for both otoscopes and ophthalmoscopes can be integrated into a single package.

An advantage realized by the present invention is that medical students or other potential users of the medical instrument can begin training in the use of the medical diagnostic device immediately upon receipt and without having to procure or access a sophisticated anatomical model of an eye or ear. The integrated teaching aids do not require assembly or manufacture to enable use. In addition, no optics other than those of the at least one medical diagnostic instrument are required.

Another advantage provided is a single package enables training with one or more medical diagnostic devices. A plurality of teaching images can be made available on separate cards to provide a training library, wherein updated training cards can be provided as needed.

Still another advantage is that the packaging includes a sales demonstration aid depicting an improved field of view that is obtainable by the packaged medical diagnostic device. In addition, the aid provides a comparison of the packaged medical diagnostic device with that of prior devices of the same type.

Yet another advantage is that the packaging having the teaching aid is reusable, providing ecological benefits, wherein the packaging protects the medical diagnostic device during shipping for training, and eliminating the need to immediately discard the package.

Further features and advantages of the invention will be readily apparent from the following Detailed Description, which should be read in conjunction with the accompanying drawings.

DETAILED DESCRIPTION

The following description is directed to various embodiments of a package for a diagnostic medical device or instrument and/or instrument supplies in which the package includes an integrated simulator or teaching aid for the packaged device and/or supplies. The embodiments described herein relate to specific diagnostic devices (e.g., otoscopes and ophthalmoscopes), but it will be readily apparent to those of sufficient skill that packages for other medical devices can be similarly configured, embodying the inventive concepts described herein. In addition, certain terms are used throughout this description to provide an adequate frame of reference with regard to the accompanying drawings. These terms, which include "front", "top", "bottom", "rear", "back", "side", "interior", "inner", "exterior", "outer", "distal" and "proximal, among others, are not intended to overly constrain the scope of the invention except where so specifically noted.

Figure 1:
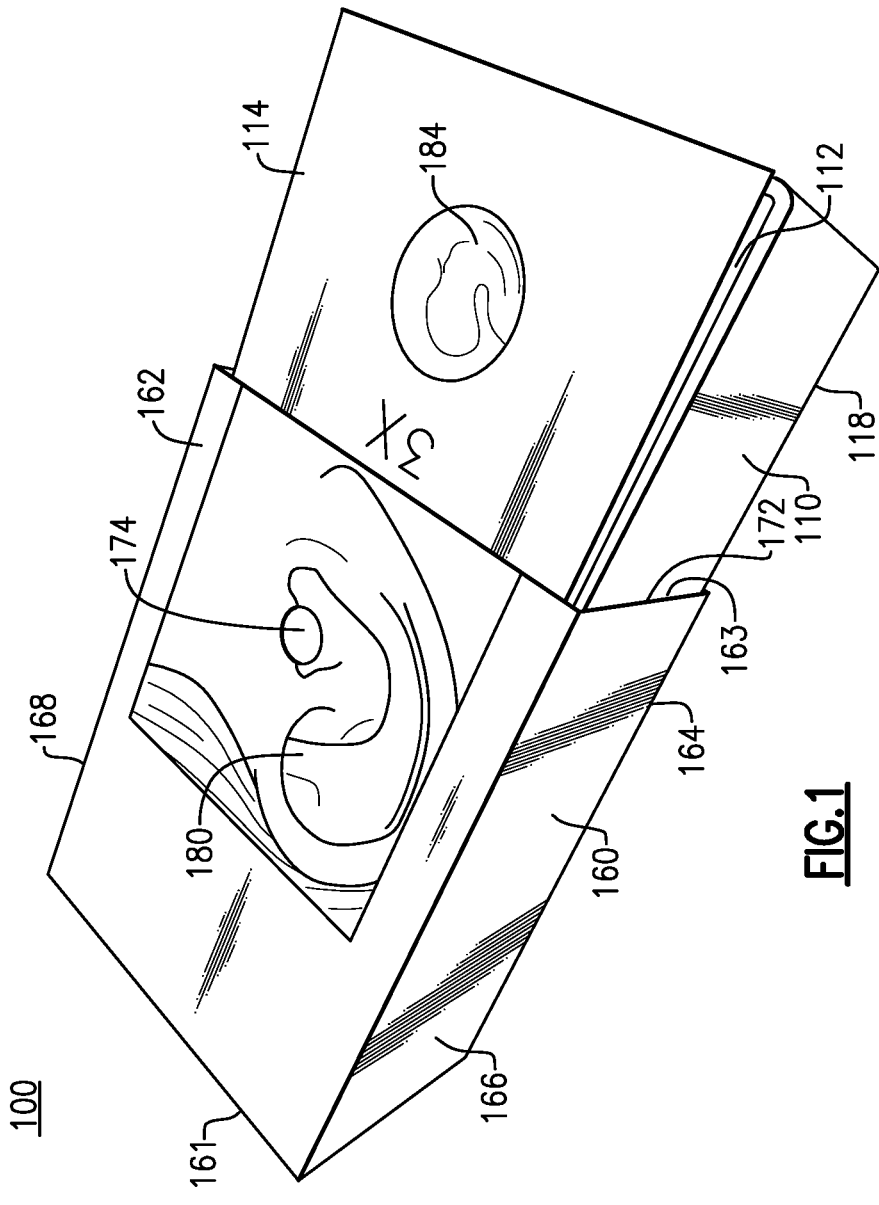
FIG. 1 is a front perspective view of a package having an integrated teaching aid made in accordance with aspects of the present invention.
Figure 2A:
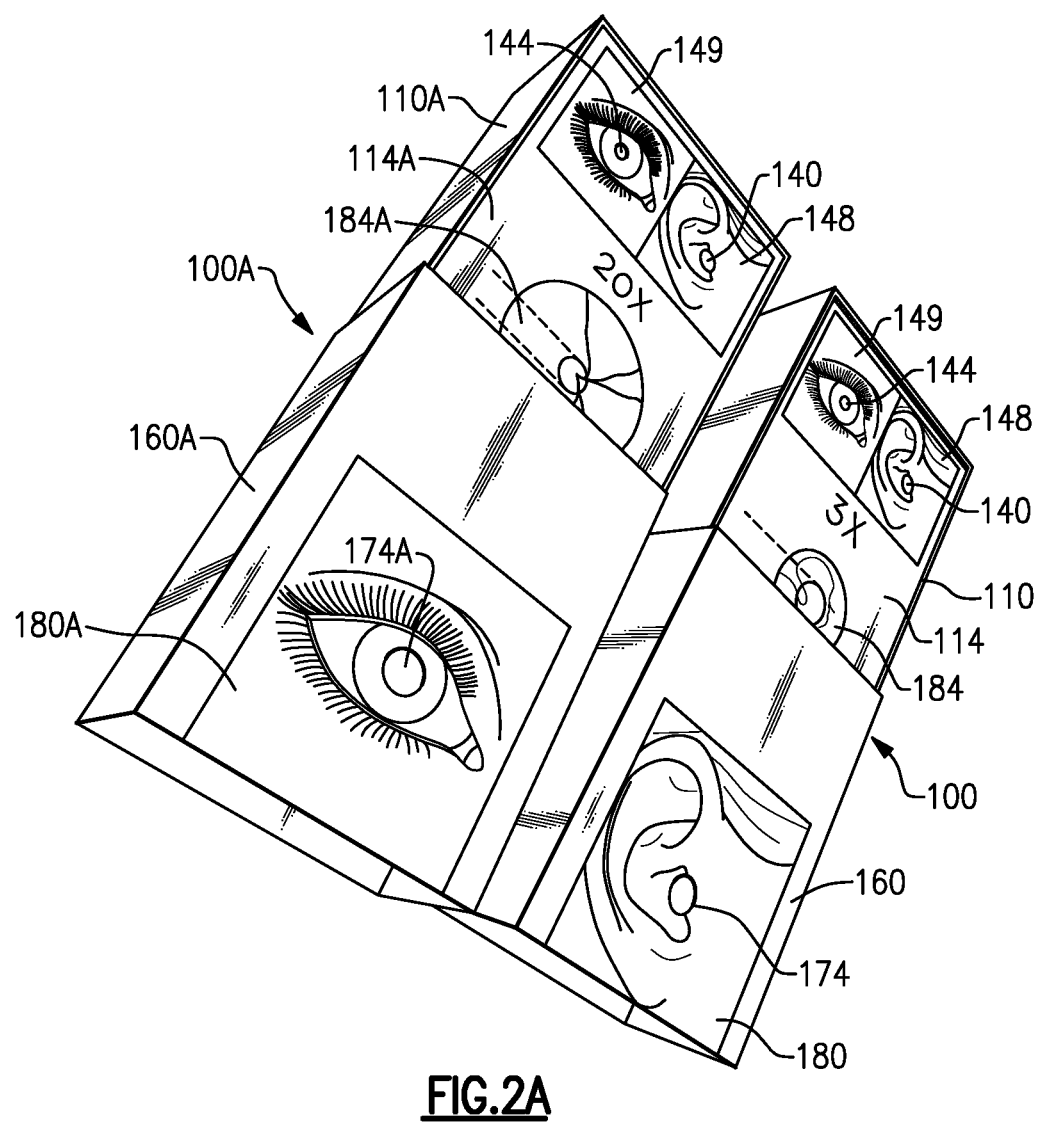
FIG. 2A is a front perspective view of the package of FIG. 1, taken alongside another package made in accordance with aspects of the invention.
Figure 2B:
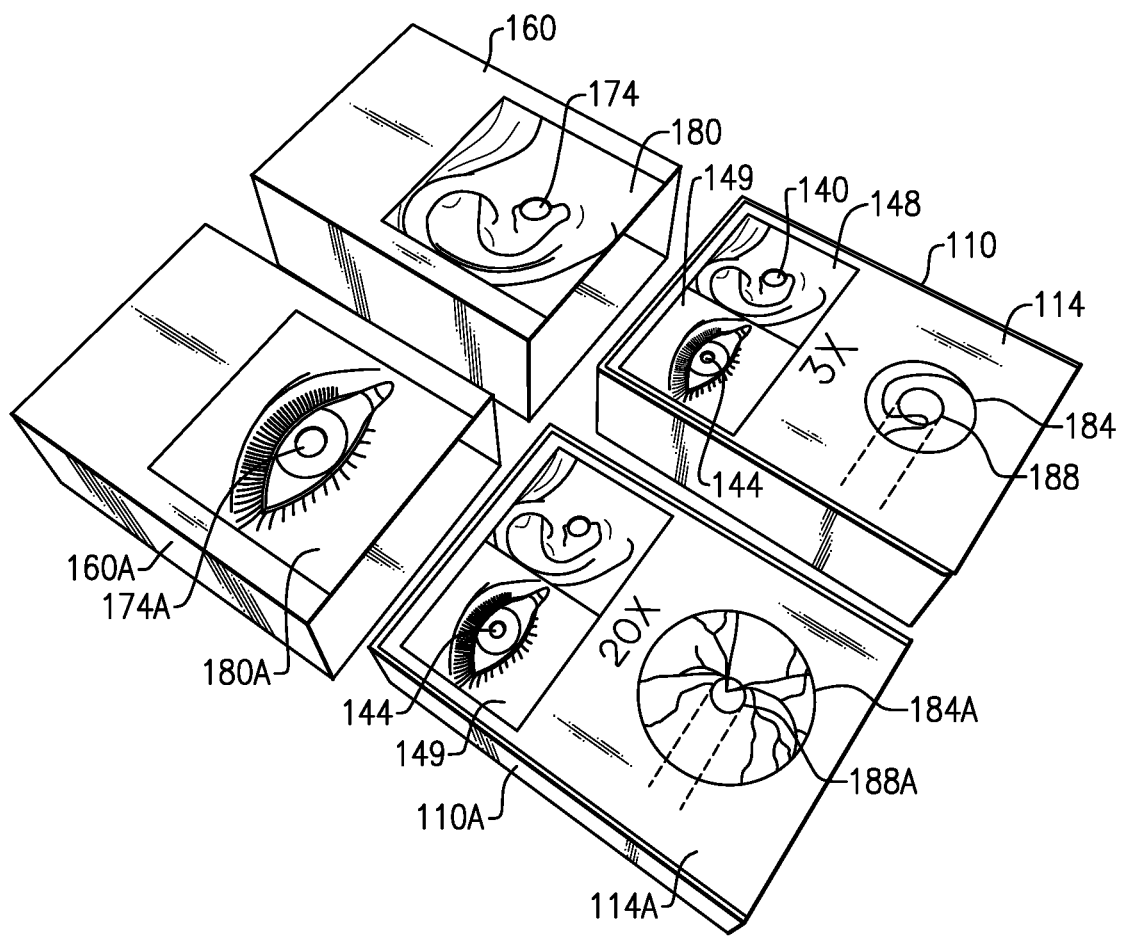
FIG. 2B is the front perspective view of the packages of FIG. 2A, with the sleeve portion completely removed from the box portion of each package.
Figure 3:
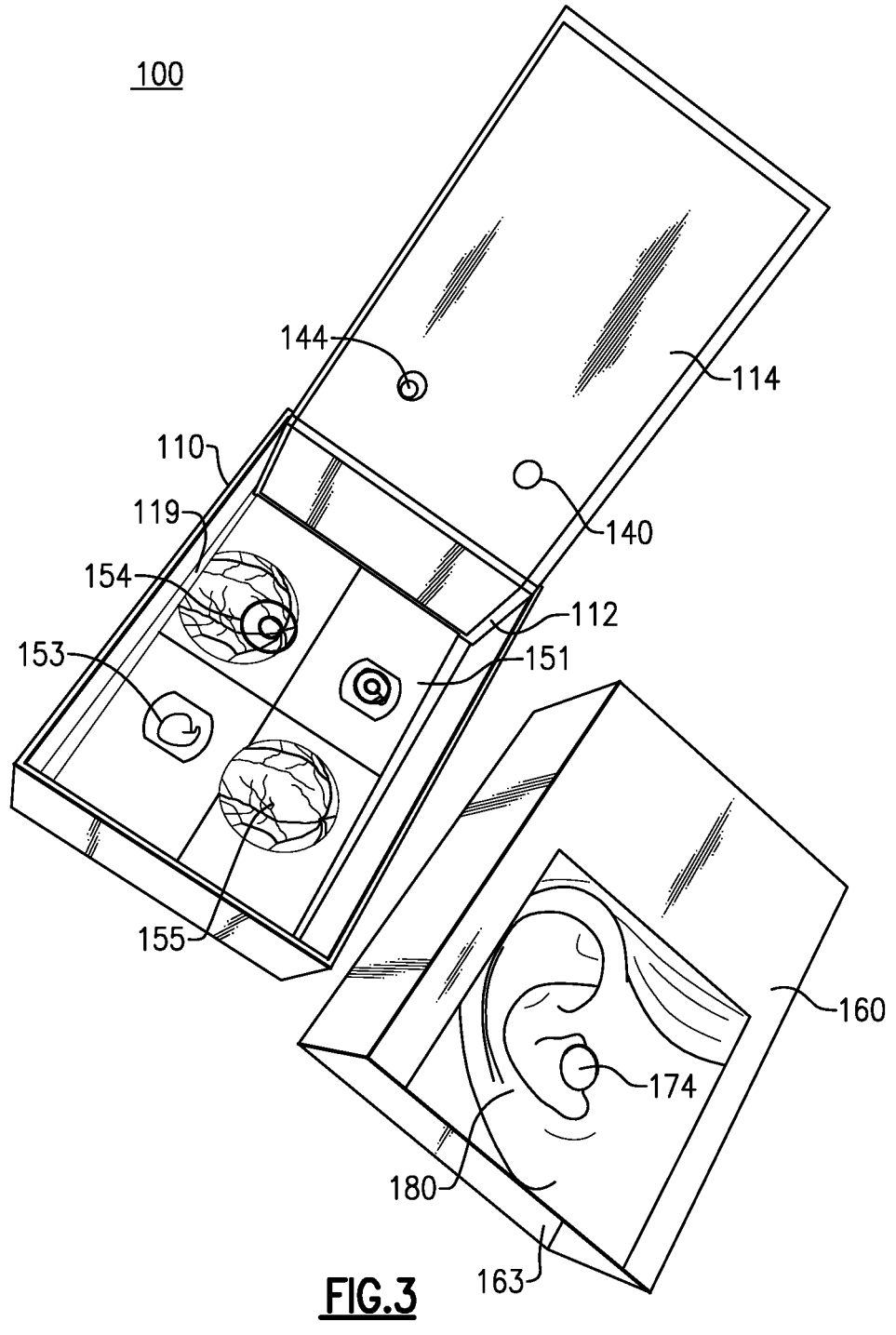
FIG. 3 depicts a partial view of the box portion of the package of FIG. 1, including a hingable front cover and a training card having multiple teaching images disposed in a defined enclosure of the box portion.

Referring to FIGS. 1-3, there is shown a package 100 for a medical diagnostic instrument or device in accordance with an exemplary embodiment. The package 100 is defined by a box portion 110 and an optional, removable sleeve portion 160. The box portion 110 is formed from a sturdy cardboard and defined in its formed condition by a front wall or cover 114, a rear wall 118, a top wall 122, a bottom wall 126 and respective side walls 130, 134. Each of the walls 114, 118, 122, 126, 130, 134 are defined by a planar configuration that combine to form an enclosure 112, which is sized and configured to retain at least one medical diagnostic instrument. The package 100 can also be configured to retain at least one of a medical diagnostic instrument and/or instrument supplies. According to this embodiment, the packaged diagnostic instrument is a portion of an otoscopic instrument (an instrument head not shown in this view), but it will be understood that other diagnostic instruments and/or instrument supplies can be similarly retained within a suitably sized package, for example, a package 100A suitably sized and configured for retaining an ophthalmoscope instrument head, as shown in FIGS. 2A and 2B.

Each of the walls 114, 118, 122, 126, 130, and 134 of the box portion 110 are further defined by respective outer and inner surfaces. According to this specific embodiment and as shown more specifically in FIG. 3, the front wall or cover 114 of the box portion 110 is hingably attached to the top wall 122 to enable access to the defined enclosure 112, and removal of the retained medical diagnostic instrument (not shown in that view).

Integrated Teaching Aid

The herein described package 100 is equipped with an integrated teaching aid that includes one or more teaching images in order to model or simulate a medical target (e.g., the middle ear or a nasal cavity for an otoscope, a retina for an eye, etc.) that is viewable by at least the packaged medical diagnostic instrument. According to this exemplary embodiment and with continued reference to FIGS. 1-3, the front wall 114 of the box portion 110 includes a pair of through openings 140, 144 in spaced relation adjacent one end. In the present embodiment, each of the through openings 140, 144 are disposed adjacent the top end 122 of the box portion 110. It will be readily understood that the positioning of the openings 140, 144 relative to the box portion 110, 110A of the package 100, 100A can be suitably varied.

In each package 100, 100A, the through openings 140, 144 are formed in relation to pictorial representations of the outer ear 148 and eye 149, respectively, that are printed or otherwise provided on the outer surface of the front cover 114 of the box portion 110. As best shown in FIG. 1, the through opening 140 is disposed in relation to the ear canal of the representative image 148 in which the through opening 140 has a diameter representative of an average ear canal of a human subject (e.g., about 5 mm) such that the target is in good focus during use. As further shown in FIG. 6, the through opening 140 replicating the ear canal is appropriately sized to receive the distal end of a truncated conical speculum tip 220 of an otoscope 210 in which the speculum tip 220 can be inserted up to a predetermined distance within the defined enclosure 112 of the package 100, 100A.

Figure 7:
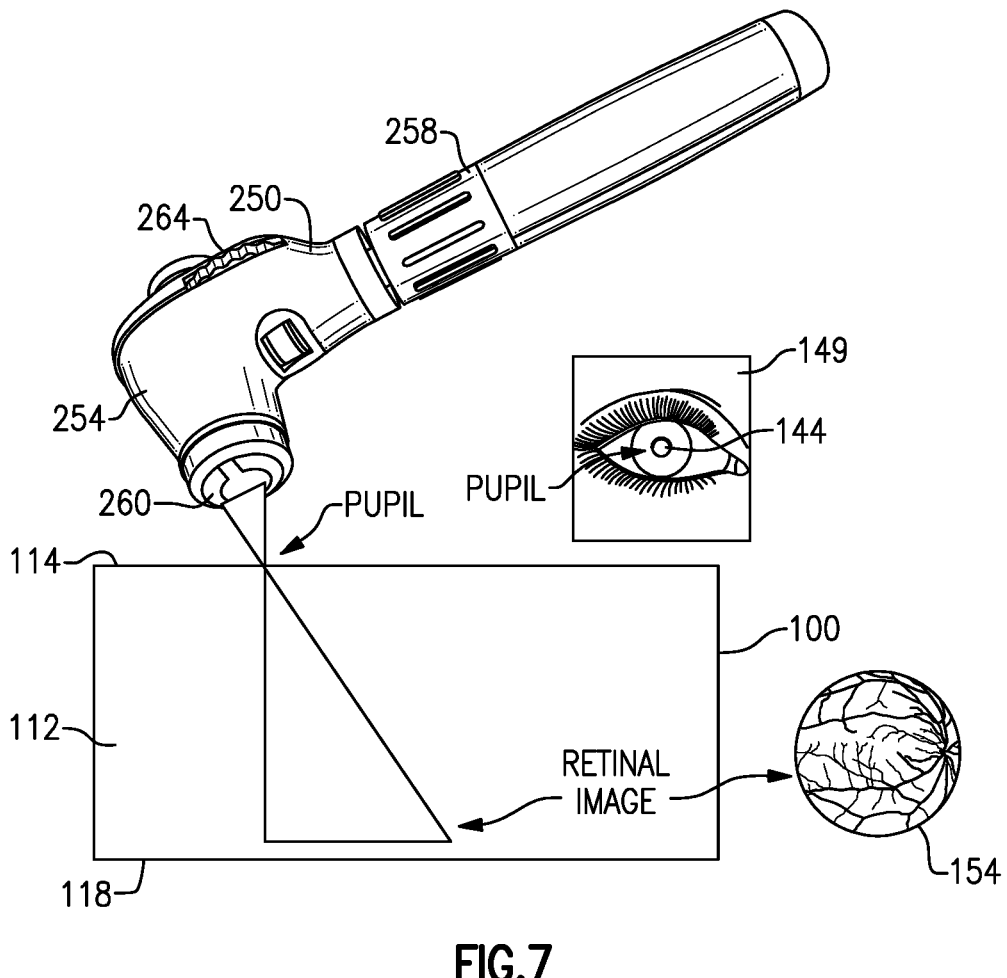
FIG. 7 is a diagrammatic view of another medical diagnostic device used with an integrated training aid made according to aspects of the present invention.

According to this specific embodiment and with reference to FIGS. 2A, 2B and 7, the adjacent opening 144 formed in the front cover 114 of the box portion 110 is configured in relation to the pictorial representation of the eye 149 and more specifically the pupil, wherein the opening 144 is configured for alignment with the distal end of an ophthalmoscope 250. This opening 144 is sized to match a tightly constricted pupil, commonly seen by clinicians, such as approximated 3-4 mm. This exemplary size is one that is typically seen, but also difficult to examine, except with devices designed for non-mydriatic use. This size also illustrates the proper working distance, since only at this distance can the user see the fully expected view of the retina.

Figure 4:
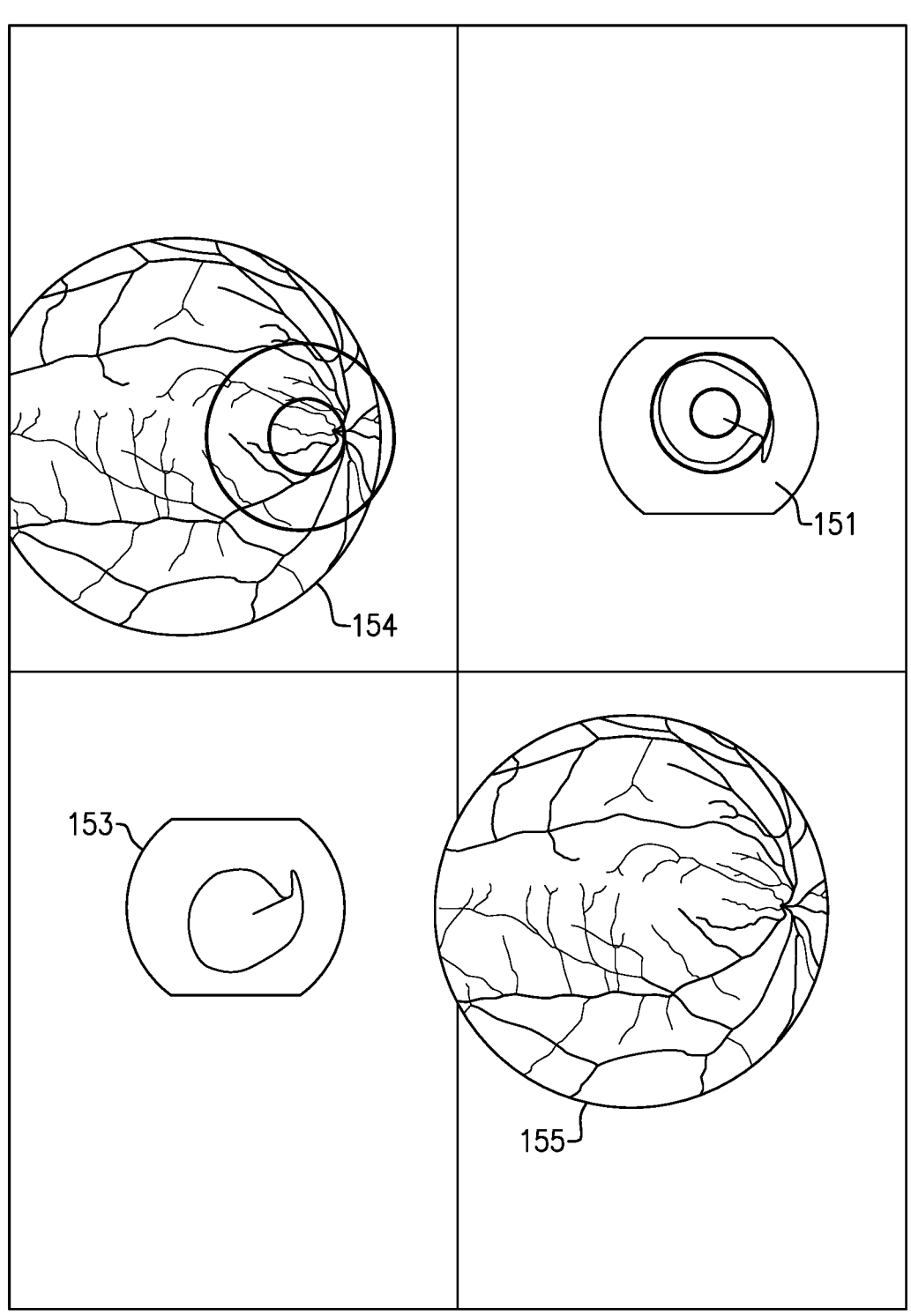
FIG. 4 is an enlarged plan view of the training card shown in the package of FIG. 3.

With reference to FIGS. 3 and 4, the rear wall 118 of the box portion 110 includes an inner surface 119 on which at least one training card 150 can be disposed. According to at least one version, a training card 150 preferably includes at least one teaching image of a portion of a medical target. According to this specific embodiment, the training card 150 includes four (4) teaching images and more specifically first and second teaching images 151, 153 of the middle ear (tympanic membrane), shown in the upper right and lower left quadrants of the training card 150 and first and second teaching images 154, 155 of the eye disposed in the upper left and lower right quadrants, respectively.

Figure 6:
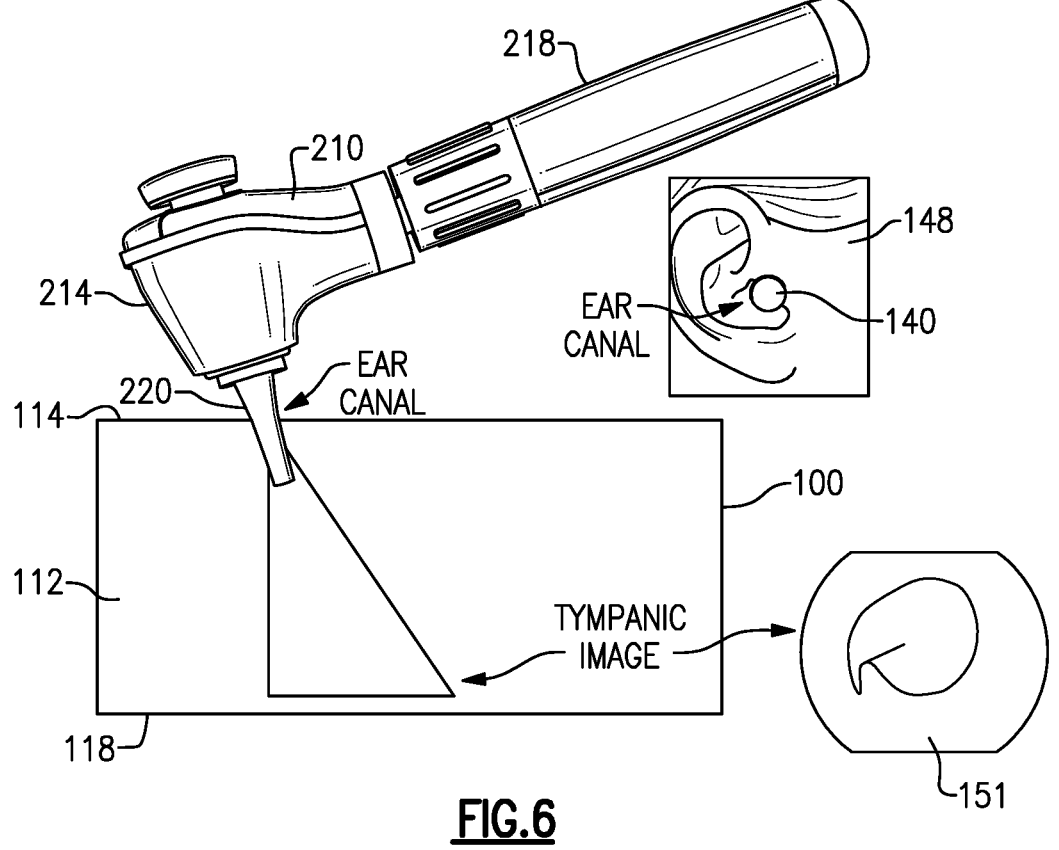
FIG. 6 is a diagrammatic view of a medical diagnostic device used with an integrated package training aid made according to aspects of the present invention.

When placed in the defined enclosure 112 of the box portion 110, the first teaching image 151 (e.g., the tympanic membrane) is aligned with the opening 140 formed in the front cover 114 of the box portion 114 and the first teaching image 154 of the eye is aligned with the adjacent opening 144 as diagrammatically shown in FIGS. 6 and 7, respectively. Preferably and when positioned, each teaching image 151, 154 is aligned at a slight downward angle relative to the center axis of the formed openings 140, 144 to prevent or at reduce the incidence of glare produced by the light source of the positioned medical diagnostic instrument(s). No additional optics are required for viewing the images of the training card 150 using the integrated teaching aid.

To utilize the integrated teaching aid, a retaining portion (not shown) of the instrument is removed from the defined enclosure 112, leaving a hollow cavity. The retained instrument, which according to the example of FIG. 1 is an otoscopic instrument head 214 can then be used following attachment of the instrument head 214 to the upper end of an instrument handle 218 and the releasable attachment of a conically shaped speculum tip element 220 to a distal retaining portion of the instrument head 214 as shown in FIG. 6. The instrument handle 218 includes one or more batteries for powering a light source (at least one LED) disposed within the instrument head 214, when attached, the instrument handle 218 having a rheostat for controlling the amount of illumination emitted using optical fibers extending to a distal opening of the instrument head 214 surrounding the speculum tip 220. The speculum tip 220 for use with the housed otoscope 210 can be made from an optically translucent material that enables both axial and circumferential illumination. According to one version, a smart device (not shown), such as a smart phone, can be attached to a proximal end of the instrument head 214 in a manner such that the optical system of the smart device is aligned with the optical axis of the medical diagnostic device. Additional details regarding an exemplary otoscope are described in U.S. Patent Application Publication No. 2019/0216307 A1, which is incorporated herein in its entirety. The distal end of the speculum tip 220 is then positioned to a predetermined distance within the defined opening 140 in a manner similar to that of typical patient use and aligned with the teaching image 151 of the training card 150. The otoscope 210, is designed for close focus and the design of the integrated teaching aid insures a good focus with the teaching images of the training card 150.

Similarly and as shown in FIG. 7, the ophthalmoscope such as 250 includes an instrument head 254 that is attachable to an instrument handle 258 containing one or more batteries for powering a contained light source, such as one or more LEDs. The distal end 260 of the ophthalmoscope 250 is aligned with the opening 144 formed in the front cover 112 and adjusted for close focus using its focus mechanisms, much like that as is required on some eye simulators in order to adequately view the retinal image 154 on the disposed training card 150. For example, an ophthalmoscope may be adjusted to focus with the 10 diopter lens on its focus wheel 264. Additional details regarding an exemplary ophthalmoscope are described in U.S. Patent Application Publication No. 2019/0216307 A1, which is incorporated herein in its entirety.

Figure 5:
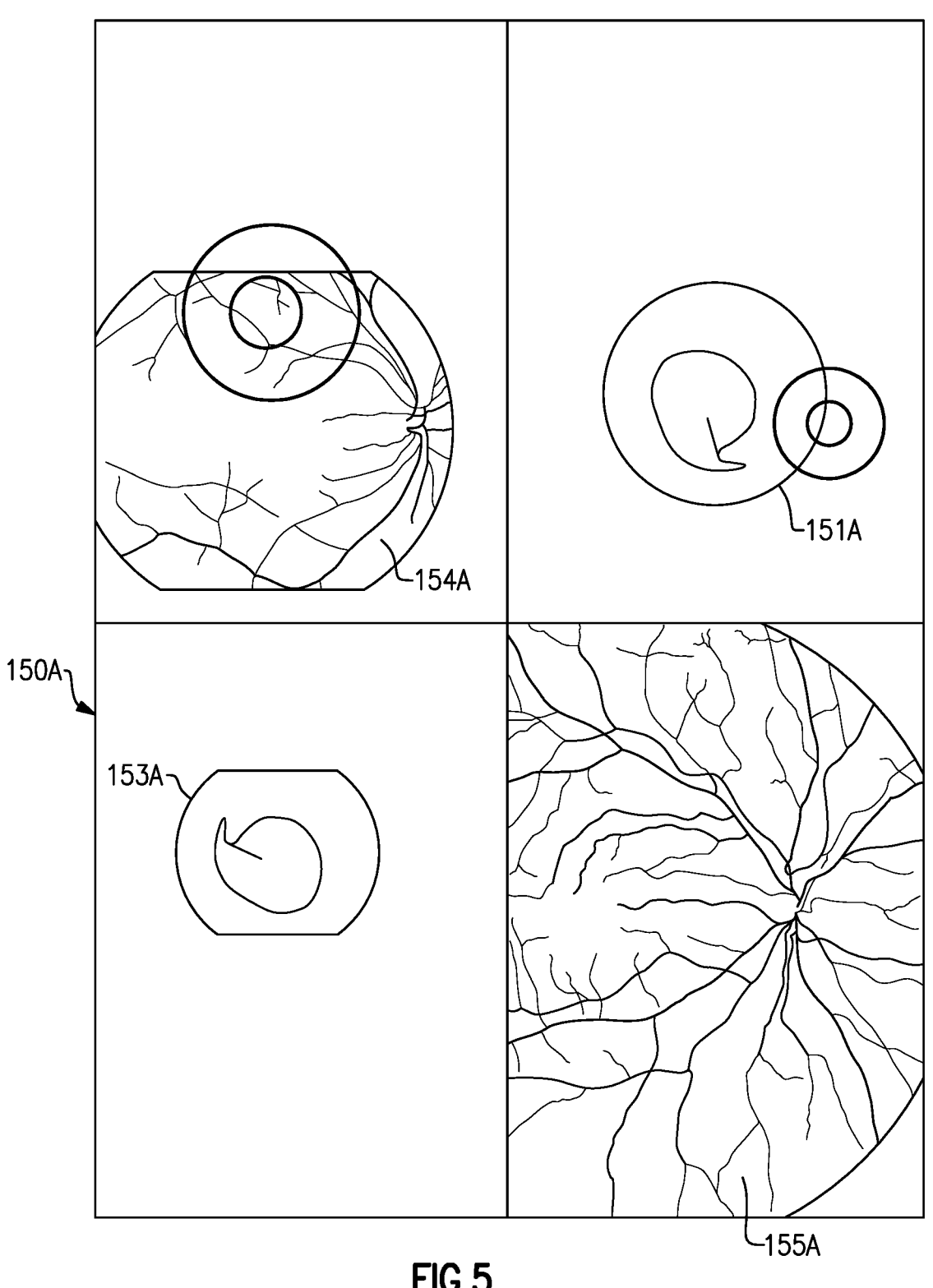
FIG. 5 is an enlarged view of a training card made in accordance with another embodiment.

The second teaching images 153, 155 of the eye and ear can be alternatively used and aligned with the openings 140, 144 by removing the training card 150 from the defined enclosure 112 and rotating the training card 180 degrees. Additional teaching images can be provided, for example on the reverse side of the training card 150 or as shown in FIGS. 4 and 5, a plurality of training cards 150, 150A can be provided that can be used interchangeably in conjunction with one or more medical diagnostic instrument(s). For example, a teaching image can be provided representative of the optic disc or other aspects of the back of the eye for purposes of training. According to yet another version, at least one of the training cards positioned in the back of the herein described box package can include a visual acuity chart and/or a pupil gauge. It will be understood that other variations can be contemplated.

According to an alternative although less preferable embodiment, one or more teaching images (not shown) can be directly applied to the inner surface 119 of the rear wall 114 of the box portion 110. The teaching images 151, 154 are designed to train the user in observing specific features, including various anomalies or conditions and can further be provided with alignment aids or other denotations for training purposes. As previously noted, it will be understood that the number of training cards 150, as well as the number of teaching images provided on each training card 150, 150A can be suitably varied. For example and according to one version, a total of four (4) teaching images of the middle ear can be provided on a single training card or additional views of other medical targets (e.g., the nasal cavity or throat for use with an otoscope). It is understood that other suitable configurations will be readily apparent. Additionally, training cards can be customized to include logos and details, such as in conjunction with specific medical schools as a means for promoting their programs.

Sales Demonstration Aid

With reference to FIGS. 1, 2A and 2B, the removable sleeve portion 160 of the herein described package 100 (as well as the sleeve portion 160A of device package 100A) is defined by a an open top end 161 and an open bottom end 163, as well as a front wall 162, a rear wall 164 and respective side walls 166, 168 that are sized for placement over the box portion 110. The walls 162, 164, 166, 168 are commonly defined by a thin planar and rectangular shape and made from a paper stock or similar material that can be formed into a unitary structure having a through opening or cavity 172 extending from the open top end 161 to the open bottom end 163 of the sleeve portion 160. The cavity 172 is sized to fit in overlapping fashion onto the box portion 110 of the package 100.

According to this exemplary embodiment, the front wall 162 of the sleeve portion 160 includes a through opening 174 adjacent the open bottom end 163 that is disposed in relation to a pictorial representation or image 180 displayed on the outer surface of the sleeve portion 160. In the depicted embodiment, the image 180 is that of the medical target to be examined by the packaged medical diagnostic instrument. In the exemplary embodiment, the image 180 is that of the outer ear for sleeve portion 160 of package 100 retaining an otoscope and the image 180A is that of the eye for sleeve portion 160A of package 100A retaining an ophthalmoscope. The through openings 174, 174A of each sleeve portion 160, 160A is aligned with another pictorial representation 184, 184A formed on the outer surface of the front cover 114, 114A of the box portion 110 when the sleeve portion 160, 160A is engaged over the box portion 110, 110A. More specifically, the images 184, 184A represent the expected field of view of an image of the medical target (e.g., the middle ear for image 184 and the retina for image 184A) obtainable by the packaged medical diagnostic instrument. Only a fractional portion of the image 184, 184A can be seen through the opening 174 of the sleeve portion 160, 160A, wherein the portion of the image 180, 180A viewable through the opening 174 represents the field of view that can be viewed using a standard otoscope. In at least one version, the differences can be further shown by the inclusion of a printed circle 188, 188A disposed at the center of the image 180, 180A to further demonstrate the differences in expected field of view. For the exemplary packages 100 and 100A, aspects of the improved and packaged otoscope 210 and ophthalmoscope 250 are described in greater detail in U.S. Patent Application Publication No. 2019/0216307 A1, which is herein incorporated by reference in its entirety.

PARTS LIST FOR FIGS. 1-7

100 package
100A package
110 box portion
110A box portion
112 enclosure
114 front wall or cover, box portion
114A front wall or cover, box portion
118 rear wall, box portion
122 top wall, box portion
126 bottom wall, box portion
130 side wall, box portion
134 side wall, box portion
140 through opening, first
144 through opening, second
148 image, outer ear
149 image, eye
150 training card
151 first teaching image, ear
153 second teaching image, ear
154 first teaching image, eye
155 second teaching image, eye
160 removable sleeve portion
160A removable sleeve portion
161 open top end, sleeve portion 162 front wall, sleeve portion
163 open bottom end, sleeve portion
164 rear wall, sleeve portion
166 side wall, sleeve portion
168 side wall, sleeve portion
172 cavity, sleeve portion
174 through opening, sleeve portion
180 pictorial image, sleeve portion
180A pictorial image, sleeve portion
184 representative image, front cover
184A representative image, front cover
188 field of view
188A field of view It will be understood that various modifications can be made to the embodiments discussed in this application that still embody the inventive aspects, as defined in accordance with the following claims.

The invention claimed is:

1. A medical diagnostic instrument training and packaging system, said system comprising:
   a package having an enclosure sized and configured for retaining at least one of a medical diagnostic instrument and instrument related supplies and accessories, wherein the package comprises a box portion having a front wall, a top wall, a rear wall, a bottom wall and respective side walls defining the enclosure, the front wall including one or more formed openings adapted to receive or be aligned with a distal end of a medical diagnostic instrument;
   a teaching aid for use with the medical diagnostic instrument, the teaching aid being at least partially integrated in the package; and
   at least one training card insertable in the package against the rear wall within the defined enclosure, the at least one training card having one or more teaching images aligned with the one or more formed openings in the front wall of the box portion.

2. The system according to claim 1, wherein the rear wall includes at least one teaching image of a medical target.

3. The system according to claim 1, wherein the medical diagnostic instrument comprises one of an otoscope or an ophthalmoscope.

4. The system according to claim 1, wherein the one of more formed openings comprises a pair of openings formed on the front wall, each of the openings optically aligned with the at least one teaching image.

5. The system according to claim 1, wherein the at least one teaching image is aligned at an angle relative to a center axis of the formed openings in order to minimize glare.

6. The system according to claim 1, wherein at least one of the one or more teaching images include comparative field of views of a medical target that are obtained by different medical instruments of the same type.

7. The system according to claim 1, wherein the package further comprises a removable sleeve configured to cover the front, rear and side walls of the box portion, the sleeve including an opening formed in a front wall aligned with an image of a medical target disposed on an outer surface of the front wall of the box portion.

8. A package for a medical diagnostic instrument, said package comprising:
   a box portion capable of retaining at least one of a medical diagnostic instrument and instrument supplies, the box portion comprising a front wall, a top wall, a rear wall, a bottom wall and respective side wall defining an enclosure, wherein the front wall includes one or more openings adapted to received or be aligned with a distal end of one of more medical diagnostic instruments; and
   a teaching aid integrated within the package; and
   a removable sleeve portion sized and configured to cover the front, rear and side walls of the box portion, the sleeve portion including an opening aligned with a representation of an image of a medical target on an outer surface of the front wall of the box portion.

9. The package according to claim 8, wherein the rear wall within the package includes at least one teaching image of a medical target typically viewed by the one or more medical diagnostic instruments.

10. The package according to claim 9, wherein the one or more openings are aligned relative to said at least one teaching image, and in which the at least one teaching image is disposed at an angle relative to a center axis of the one or more openings in order to minimize glare.

11. The package according to claim 8, including a pair of through openings on the front wall of the box portion, each of the through openings replicating an eye or ear.

12. The package according to claim 11, further comprising at least one training card insertable in the package against an inner surface of the rear wall, the at least one training card having one or more said teaching images.

13. The package according to claim 12, wherein at least one of the one or more teaching images include comparative field of views of a medical target that are obtained by different medical instruments of the same type.

14. The package according to claim 12, wherein the one or more teaching images include representative images of medical targets taken by the medical diagnostic instrument.

15. A method for training individuals in the use of at least one medical diagnostic instrument, said method comprising:
   providing a box-like package, the box-like package defining an enclosure sized for retaining at least one of a medical diagnostic instrument and instrument supplies, the package having a front wall, a back wall, a top wall, a bottom wall and respective side walls, the package having one or more formed openings in the front wall, each formed opening being sized and configured for alignment with at least one medical diagnostic instrument; and
   integrating a teaching aid in the package to simulate one or more medical targets viewable by the at least one medical diagnostic instrument by disposing one or more teaching images of a medical target on the rear wall of the box portion within the enclosure of the package, in which the one or more teaching images are aligned with the one or more formed openings and in which the disposing one or more teaching images comprises at least one training card insertable in the package against the rear wall within the defined enclosure, the at least one training card having one or more teaching images aligned with the one or more formed openings in the front wall of the box portion.

16. The method according to claim 15, wherein the one or more medical diagnostic instruments include at least one of an ophthalmoscope and an otoscope.

17. The method according to claim 15, in which two or more formed openings are provided and in which each opening is configured for alignment between a teaching image and a medical diagnostic instrument.

18. The method according to claim 15, further comprising providing a removable sleeve portion sized and configured to cover the front, rear and side walls of the box portion, the sleeve portion including an opening aligned with a representation of an image of a medical target on an outer surface of the front wall of the box portion.

\* \* \* \* \*